United States Patent
Ehlis et al.

(10) Patent No.: US 6,369,268 B1
(45) Date of Patent: Apr. 9, 2002

(54) DIESTER AMINE ADDUCTS

(75) Inventors: Thomas Ehlis, Freiburg; Peter Frankhauser, Ettingen; Dietmar Hüglin, Eimeldingen, all of (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/530,537

(22) PCT Filed: Oct. 27, 1998

(86) PCT No.: PCT/EP98/06811

§ 371 Date: May 1, 2000

§ 102(e) Date: May 1, 2000

(87) PCT Pub. No.: WO99/24392

PCT Pub. Date: May 20, 1999

(30) Foreign Application Priority Data

Nov. 6, 1997 (EP) .............................. 97810833

(51) Int. Cl.$^7$ ...................... C07C 229/00; C07C 211/00
(52) U.S. Cl. ...................... 560/169; 560/344; 560/129; 562/566; 564/511
(58) Field of Search ................. 560/344, 169, 560/129; 562/566; 564/511

(56) References Cited

U.S. PATENT DOCUMENTS

| | | | |
|---|---|---|---|
| 3,979,442 A | * | 9/1976 | Schafer et al. |
| 5,633,336 A | | 5/1997 | Gras et al. .................. 528/68 |
| 5,652,301 A | | 7/1997 | Schmitt et al. ............. 524/591 |

FOREIGN PATENT DOCUMENTS

| | | | |
|---|---|---|---|
| DE | 2341045 | | 3/1974 |
| EP | 0710656 | | 5/1996 |
| GB | 2299809 | * | 10/1996 |

OTHER PUBLICATIONS

Chem. Abstr. vol. 90, No. 21, May 21, 1979, Abstr. No. 168021 for Zh. Org. Khim., vol. 14, No. 11, 1978, pp. 2252–2258, Tanchuk et al.*

Chem. Abstr. vol. 85, No. 3, Jul. 19, 1976, Abstr. No. 20570u for Ukr. Khim. Zh., vol. 42, No. 4, 1976, pp. 390–394, Tanchuk et al.*

* cited by examiner

*Primary Examiner*—Ralph Gitomer
*Assistant Examiner*—Devesh Khare
(74) *Attorney, Agent, or Firm*—Kevin T. Mansfield

(57) ABSTRACT

Described are diester amine adducts of formula (1) wherein $R_1$, $R_2$, $R_3$, $R_4$ are each independently of one another $C_4$–$C_{22}$alkyl; $C_2$–$C_{22}$alkenyl; or $C_5$–$C_7$cycloalkyl; $X_1$ and $X_2$ are each independently of the other hydrogen, $C_1$–$C_4$alkyl; $C_2$–$C_4$hydroxyalkyl or $C_2$–$C_4$hydroxyhaloalkyl; Y is a radical of formula (1b); $A_1$ is $C_2$–$C_3$alkylene or 2-hydroxy-n-propylene; $X_3$ is hydrogen; $C_1$–$C_4$alkyl, $C_2$–$C_4$hydroxyalkyl; or $C_2$–$C_4$hydroxyhaloalkyl; (A) is an asymmetrical carbon atom in the R- or S-configuration, wherein, if $C^1$=R, $C^2$=R; $C^1$=S, $C^2$=S; and $C^1$=R; $C^2$=S; $m_1$ is 1 or 2; and n is an integer from 1 to 4; p is 0 or 1; which adducts may be in the form of free bases or ammonium salts. Said compounds are precursors of compounds having good complex-forming properties and are thus able to effectively bind heavy metal ions such as iron, zinc, magnesium or copper ions and to prevent metal-initiated oxidations after enzymatic or chemical cleavage. They have a plurality of uses, for example in foods, beverages, derusting and decalcification baths, as additives in liquids for cooling-water circuits, in personal-care products, as bleaching stabilizers, in cleaning agents and detergents, in the textile industry and also as soft handle agents for organic fibre materials.

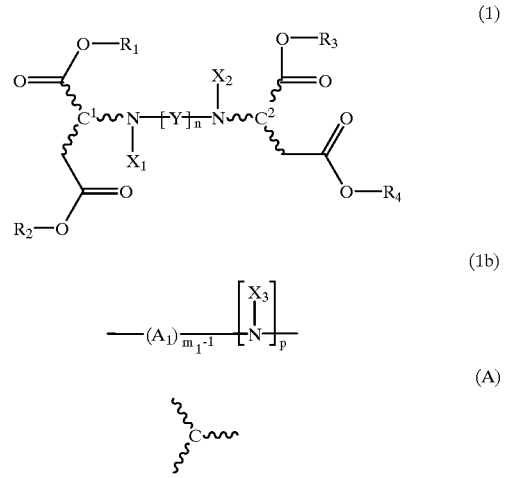

9 Claims, No Drawings

DIESTER AMINE ADDUCTS

The present invention relates to diester amine adducts, to a process for the preparation of these compounds and to their use.

The diester amine adducts of this invention correspond to formula

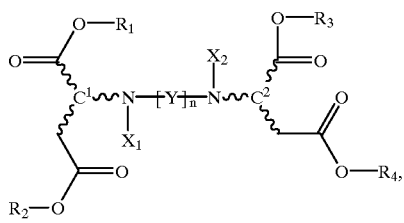

(1)

wherein $R_1$, $R_2$, $R_3$, $R_4$ are each independently of one another $C_4$–$C_{22}$alkyl; $C_2$–$C_{22}$alkenyl; or $C_5$–$C_7$-cycloalkyl;

$X_1$ and $X_2$ are each independently of the other hydrogen, $C_1$–$C_4$alkyl; $C_2$–$C_4$hydroxyalkyl or $C_2$–$C_4$hydroxyhaloalkyl;

Y is a radical of formula (1b)

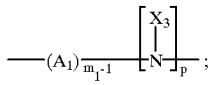

$A_1$ is $C_2$–$C_3$alkylene or 2-hydroxy-n-propylene;

$X_3$ is hydrogen; $C_1$–$C_4$alkyl, $C_2$–$C_4$hydroxyalkyl; or $C_2$–$C_4$hydroxyhaloalkyl;

is an asymmetrical carbon atom in the R- or S-configuration, wherein, if $C^1$=R, $C^2$=R;

$C^1$=S, $C^2$=S; and $C^1$=R; $C^2$=S;

$m_1$ is 1 or 2; and n is an integer from 1 to 4;

p is 0 or 1;

which adduct may be in the form of a free base, acid, acid salt or quaternary ammonium salt.

The diester amine adducts are stereochemically uniform compounds in the (SS)-, (RR)- or (RS)-configuration, i.e. compounds which can be represented by formulae

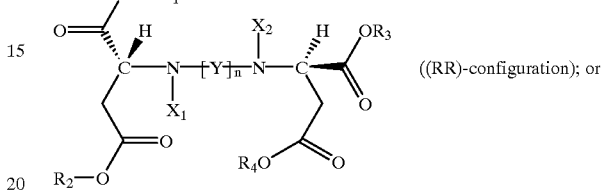

((SS)-configuration));

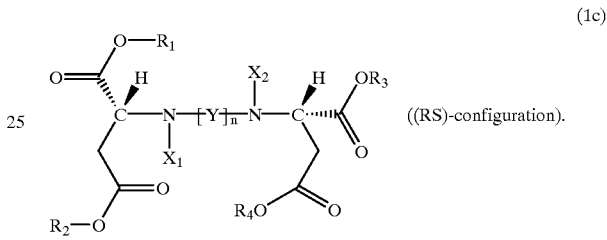

((RR)-configuration); or

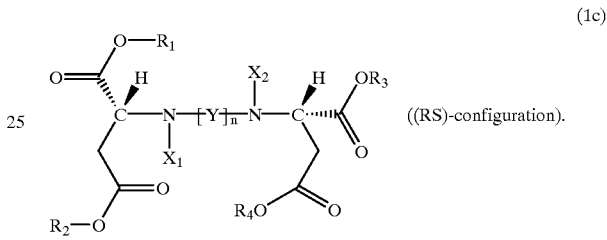

((RS)-configuration).

$C_1$–$C_{22}$Alkyl is a straight-chain or branched alkyl radical, for example methyl, ethyl, n-propyl, isopropyl, n-butyl, sec-butyl, tert-butyl, amyl, isoamyl or tert-amyl, heptyl, octyl, isooctyl, nonyl, decyl, undecyl, dodecyl, tetradecyl, pentadecyl, hexadecyl, heptadecyl or octadecyl or eicosyl.

$C_2$–$C_{22}$Alkenyl is, for example, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, iso-dodecenyl, n-dodec-2-enyl or n-octadec-4-enyl.

$C_5$–$C_7$Cycloalkyl is typically cyclopentyl, cycloheptyl or, preferably, cyclohexyl.

$C_2$–$C_4$Hydroxyalkyl is, for example, 2-hydroxyethyl or 4-hydroxy-n-butyl.

$C_2$–$C_4$Hydroxyhaloalkyl is typically 1-chloro-2-hydroxyethyl.

Preferred diester amine adducts of formula (1) are those, wherein $A_1$ is $C_2$–$C_3$alkylene;

m is 2; and p is 0.

Particularly preferred diester amine adducts of formula (1) are those, wherein $X_1$ and $X_2$ are hydrogen and very particularly preferably those, wherein $R_1$, $R_2$, $R_3$ and $R_4$ are $C_4$–$C_2$alkyl.

Examples of diester diamine adducts of this invention are the compounds of formulae (3)

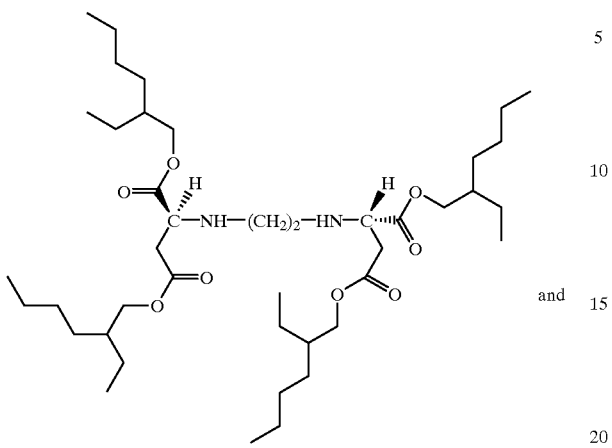

and (4)

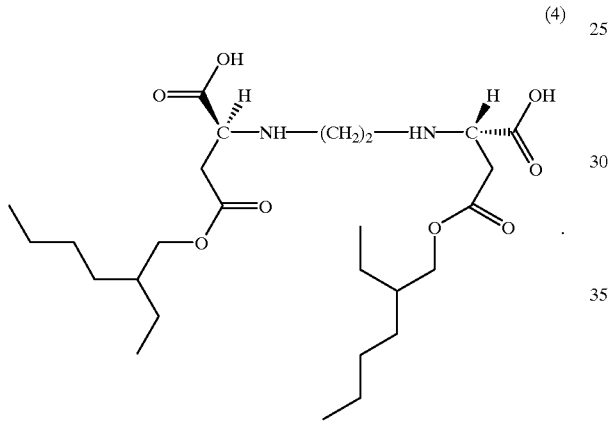

The novel diester amine adducts, which are stereochemically uniform with respect to the $C^1$ and $C^2$ atoms (see formula (1)), are prepared by methods known per se by reacting an aminodicarboxylic acid of formula

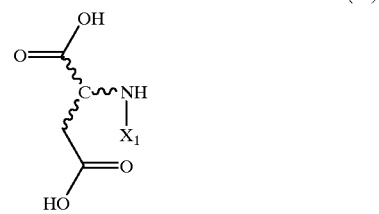

(1d)

with an excess of the relevant alcohol under the action of gaseous HCl or thionyl chloride in a one-pot reaction. Such a process is disclosed, inter alia, in C.A. 62, 11911g (1965). The corresponding diester amine adducts can be converted to the corresponding diester amine adducts of formula (1) by reacting the resultant aminodicarboxylates of formula

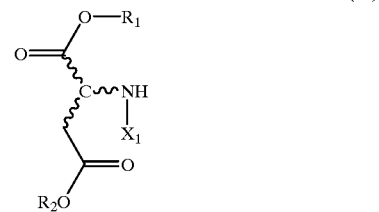

(1e)

with a dihalogen compound of formula

$Hal-(A_1)_{m-1}Hal.$ (1f)

The entire course of the reaction can be represented as follows:

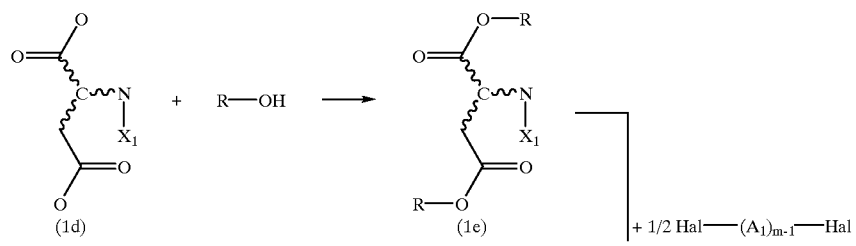

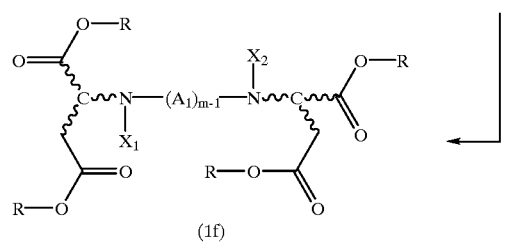

Tetraesters which are stereochemically uniform with respect to the amino carboxylic acid frameare also obtained by reacting, for example, the diaminotetracarboxylic acid of formula (1g) or the salts of this acidwith thionyl chloride and an alcohol to the corresponding ester compound of formula (1f):

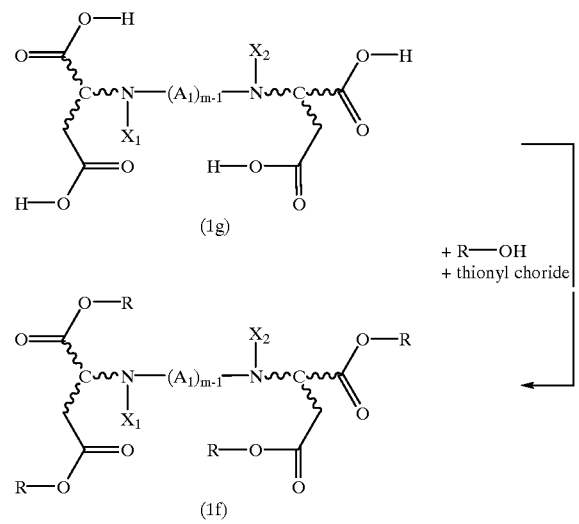

The thionyl chloride is added dropwise usually in the temperature range from −70 to 80°, preferably from −10 to 30° C. In the further course of the reaction the temperature is raised up to 200° C., the preferred temperature range being from 40 to 80° C.

Thionyl chloride is usually used in excess. In principle, thionyl chloride can also be replaced with gaseous hydrogen chloride.

After the reaction is complete, the hydrochlorides of the tetraesters may, if required, be isolated in the form of crystalline compounds and then recrystallised.

The alcohol component is used as solvent for the reaction (high excess).

The starting compound can be a water-containing tetracarboxylic acid, e.g. EDDS having a water content of about 20%.

Monoesters of the aminodicarboxylic acid can be obtained in good yields by a commonly known process by reacting the carboxylic acid with the relevant alcohol.

Mixtures of the compounds of formulae (1a), (1b) and (1c) are obtained by first esterifying maleic anhydride with an alcohol to the corresponding diester and then reacting 2 mol of the respective diester with diamine.

For many applications it is also possible to replace the stereochemically uniform products with mixtures of the stereoisomers of formulae (1a), (1b) and (1c) which are also obtained in the above manner.

The stereochemically uniform compounds of formula (1) and the diester amine adducts of formula

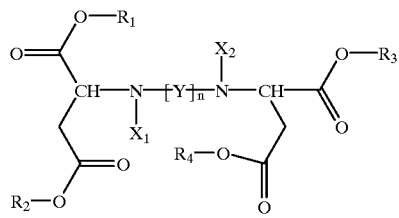

are precursors of compounds having pronounced complex-forming properties. Under physio-logical conditions, the ester groups can be split by esterases. The chemical hydrolysis is carried out in aqueous medium in the presence of $OH^-$ or $H^+$ ions. Compounds are obtained wherein $R_1=R_2=R_3=R_4=H$, for example N,N'-ethylenediamine disuccinic acid (EDDS). Such compounds are thus able to effectively bind heavy metal ions such as iron, zinc, magnesium or copper ions and to prevent metal-initiated oxidations.

In contrast to the free acids or the salts of the acids ($R_1=R_2=R_3=R_4=H$), the compounds of formula (1) are readily soluble in organic solvents, fats and oils, new fields of application being thus obtained. Said compounds are therefore suitable as additives in food and beverages products which are susceptible to oxidation and which are inclined to spoil or to become rancid. The foods susceptible to oxidation are, in particular, compounds or compositions containing olefinic double bonds.

Owing to their complex-forming properties, the novel diester amine adducts can also be used for removing undesirable calcium depositions, boiler scale and rust. They are usually used to this purpose in alkaline derusting and decalcification baths.

The novel compounds are furthermore used as additives in liquids for cooling-water circuits for preventing and dissolving calcium depositions.

The novel adducts are also used in personal-care products, for example in creams, lotions, body-care products, such as deodorants, soaps or shampoos and ointments, for preventing oxidation, rancidness, turbidity and the like.

It is possible to achieve, in particular, a soft handle effect on hair.

Furthermore, the novel diamine adducts are used as bleaching stabilisers, e.g. for sodium perborate, in detergents or in textile or paper bleaching. Heavy metal traces, for example iron, copper or magnesium, are present in detergent formulations, in water and in textile and paper materials and catalyse the degradation of sodium perborate as well as of other bleaches present in the detergent. The novel compounds bind these metal ions and prevent the undesirable degradation of the bleaching system both during storage of the corresponding detergent as well as in the washing liquor. The effectivity of the bleaching system is thus improved and fibre damage is prevented. In addition, other sensitive detergent components, such as enzymes, fluorescent whitening agents and fragrances are advantageously protected against oxidative degradation.

The novel adducts can also be used in cleaning agents and detergents for removing metal ions and as preservatives. In liquid cleaning formulations, the novel compounds may advantageously be used in a concentration of 0.05 to 15% by weight, based on the entire weight of the formulation.

The novel diester amine adducts can also be advantageously used in the textile industry for removing traces of heavy metal during production and when dyeing natural and synthetic fibres. They prevent spotty and streaky dyeings on textile material, bad wettability and unlevelness.

The novel diester amine adducts of formula (1) are also very suitable as soft handle agents for organic fibre materials such as paper or, in particular, textile fibre materials. Particularly good soft handle effects are achieved in the case of loose fibres, yarns, in particular wovens or knits of natural cellulose, e.g. cotton, or of polyacrylonitrile. These adducts can also be used to impart soft handle to fibre materials of synthetic polyamides or regenerated cellulose. Good soft handling effects are already obtained in fabric coatings of 0.1 to 1%, preferably of 0.2 to 0.6%.

Treatment of fibres is effected by treating the fibre materials with a preferably aqueous formulation, e.g. with an aqueous solution or emulsion of these adducts, applying the adducts to the fibres and then drying them. It is convenient to use 0.5 to 5%, preferably 1 to 3%, of a c. 20% emulsion or solution, based on the weight of the fibre materials to be finished. The aqueous formulations can be applied to the fibres by impregnation processes customarily used in the industry (e.g. padding or exhaust process). Solutions in organic solvents are often used via spraying.

In the same manner it is possible to treat paper webs with the novel adducts by spraying or by a dipping process, which also results in a fine and supple soft handle.

The novel diester amine adducts of formula (1) can also be used as antistatic agents for textiles, in particular for polyester fabrics.

In the paper industry, the novel compounds can be used for eliminating heavy metal/iron ions. Iron depositions on paper result in so-called hot spots as soon as the oxidative, catalytic degradation of the cellulose starts.

The novel diester amine adducts are also suitable as catalysts for organic syntheses, such as for the aerial oxidation of paraffins or for hydroformylating olefins to alcohols.

The novel diester amine adducts can be used in any desired form, for example as powder, granulate, paste, liquid formulation, tablet, capsule, pill, suspension or gel.

If the novel adducts are used e.g. as body-care products, then such a product comprises 0.01 to 15, preferably 0.5 to 10% by weight, based on the total weight of the composition, of the diester amine adduct of formula (1) or (2) as well as cosmetically compatible assistants.

Depending on the body-care product's form of it comprises other components in addition to the diester amine adduct, for example sequestrants, colourants, perfume oils, thickeners or consistency regulators, emollients, UV absorbers, skin protectives, antioxidants, additives improving the mechanical properties, such as dicarboxylic acid and/or the Al, Zn, Ca, Mg salts of $C_4$–$C_{22}$ fatty acids.

Owing to their good solubility in oil and alcohol, the novel diester amine adducts can be incorporated in the corresponding formulations without any difficulties.

A soap has, for example, the following composition:
0.01 to 5% by weight of the compound of formula (1) or (2),
0.3 to 1% by weight of titanium dioxide,
1 to 10% by weight of stearic acid,
ad 100% soap base, for example the sodium salts of tallow fatty acid and of coconut fatty acid or glycerols.

A shampoo has, for example, the following composition:
0.01 to 5% by weight of the compound of formula (1) or (2),
12.0% by weight of sodium-laureth-2-sulfate,
4.0% by weight of cocamidopropylbetaine,
3.0% by weight of NaCl, and water ad 100%.

A deodorant has, for example, the following composition:
0.01 to 5% by weight of the compound of formula (1) or (2),
60% by weight of ethanol,
0.3% by weight of perfume oil, and water ad 100%.

The following non-limitative Examples illustrate the invention in more detail. The SS-DDS used has a water content of about 20%

EXAMPLE 1

[S,S]-Ethylenediaminedisuccinic acid tetraethyl ester

Ethanol (300 g, 6.5 mol) and [S,S]-ethylenediaminedisuccinic acid (21.92 g, 0.075 mol) are placed in a vessel and thionyl chloride (53.0 g, 0.45 mol) is added dropwise at −5 to 5° C. The reaction mixture is slowly heated to room temperature and stirred for 24 h at room temperature. Subsequently, it is heated for another 12 h to 60° C. The suspension first turns into a solution and after some time the tetraester separates as hydrochloride in the form of white crystals. The suspension is diluted with 100 ml of ethanol and concentrated in a rotary evaporator at 60° C.

The white residue is suspended in a 100 g 1:1 mixture of ice/ammonia solution (25%). The aqueous phase is extracted twice with methyl-tert-butyl ether (300 ml). The organic phases are combined and then washed with water until neutral and dried over $Na_2SO_4$. Removal of the solvent under vacuum (60° C.) gives the slightly contaminated tetraester of formula (101) in the form of a colourless liquid.

The mixture can be purified by column chromatography (silica gel G60, ethyl acetate/petroleum ether [40/60] 8:2).

Yield: 20.4 g, 67% of theory $^1$H NMR (200 MHz, $CDCl_3$, TMS): δ=1.15–1.25 (m, $CH_3$, 6H), 2.0 (s, NH, 1H), 2.52–2.85 (m, $NCCH_2COO$ and $CH_2N$, 4H), 3.6 (t, NCH, 1H), 4.07–4.25-(m, $C\underline{H}_2CH_3$, 4H).

$^{13}$C NMR (200 MHz, $CDCl_3$, TMS): δ=14.48 ($CH_3$), 14.54 ($CH_3$), 38.42 ($CH_2$), 47.52 ($CH_2$), 57.79 (CH), 60.98 ($CH_2$), 61.31 ($CH_2$),171.19 ($C_q$), 173.88 ($C_q$).

(101)

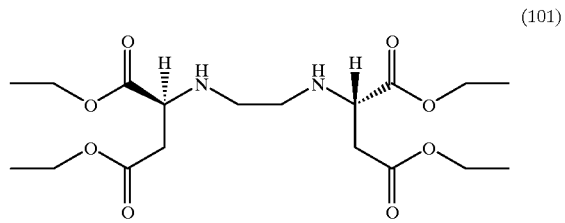

[S,S]-configuration

EXAMPLE 2

Hydrolysis of [S,S]-ethylenediaminedisuccinic acid tetraethyl ester to EDDS

[S,S]-EDDS-tetraethyl ester (1.00 g, 0.00247 mol) is suspended in 50 ml of water and thermostatted to 95° C. Using a pH controller, the pH is kept constant at 9.5–10 (1N-NaOH). After 24 h, another 50 ml of water are added and the mixture is concentrated to about 40 ml in a rotary evaporator at 80° C. The residue is transferred to a 50 ml measuring flask, filled up to the calibration mark with water and adjusted to pH=9.5. The molar specific amount of rotation of the hydrolysate is $[\alpha]^{20}_D$=−14.5.

The specific amount of rotation for a [S,S]-EDDS-trisodium salt solution prepared from L-aspartic acid and dibromoethane is $[\alpha]^{20}_D$=−15.9 (pH=9.5)

The specific amount of rotation for a [S,S]-EDDS-trisodium salt solution thermostattet for 24 h at pH=9.5–10 to 95° C. is $[\alpha]^{20}_D$=−13.8 (pH=9.5).

These meastrements show that the configuration at the asymmetrical carbon atoms in the EDDS struckue is hardly changed by the above esterification method.

EXAMPLE 3

[S,S]-/[R,R]-/[R,S]-Ethylenediaminedisuccinic acid tetraisooctyl ester (isomer mixture)

Maleic anhydride (10.1 g), 2-ethyl-1-hexanol (28.7 g) and 2.6-di(tert-butyl)-p-cresol (0.1 g) are mixed and heated to 90° C. After 2 h, 50 ml of benzene and 0.6 g of conc. sulfuric acid are added. Nitrogen is passed through and benzene and water are distilled off azeotropically. After cooling, the mixture is charged with 2.6 g of powdered sodium carbonate and stirred for 30 min. The undissolved component of the reaction mixture is removed by filtration and the filtrate is concentrated in a rotary evaporator under vacuum, giving 38 g of the crude diester of formula (103). Distillation under high vacuum gives the diester of formula (103a)

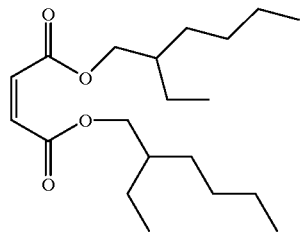

in a yield of 90% of theory.

| Elemental analysis: | | |
|---|---|---|
| | % C | % H |
| calculated: | 70.55 | 10.66 |
| found: | 70.7 | 10.9 |

After charging 100 ml of toluene with the diester of formula (103) (27.24 g, 0.08 mol), ethylenediamine (2.4 g, 0.04 mol, dissolved in 5 ml of toluene) is added dropwise at 20–25° C. and the mixture is heated for 4 h to 80 C. The solvent is removed in a rotary evaporator under vacuum. The residue is purified by column chromatography (silica gel 60, toluene/ethyl acetate 7:3).

Yield: 9.0 g, 30% of theory (yellowish liquid)

| Elemental analysis: | | | |
|---|---|---|---|
| | % C | % H | % N |
| calculated: | 68.07 | 10.88 | 3.78 |
| found: | 68.2 | 10.8 | 3.7 |

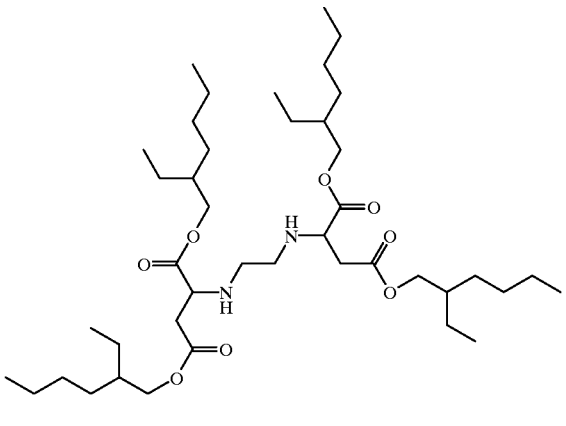

(103)

mixture of the [S,S]-, [S,R]- and [R,R]-isomers

EXAMPLE 4

[S,S]-Ethylenediaminedisuccinic acid tetraisooctyl ester

2-Ethyl-1-hexanol (100 g, 0.77 mol) is placed in a vessel and thionyl chloride (28.4 g, 0.24 mol) is added dropwise at −5 to 5° C. [S,S]-Ethylenediaminedisuccinic acid (11.68 g, 0.04 mol) is added in portions to the reaction mixture. The reaction mixture is slowly heated to room temperature and stirred for 12 h at room temperature. Subsequently, the mixture is heated for another 24 h to 60° C. and is then stirred for 48 h at room temperature. The reaction mixture is then added, with stirring, to a mixture of ice/ammonia solution and worked up as described in Example 1. To remove 2-ethyl-1-hexanol, the organic phase is concentrated under high vacuum.

This affords a yellowish oil corresponding to formula (104) of slightly contaminated tetraester (21 g, 73% of theory).

The product can be purified by column chromatography (silica gel G60, ethyl acetate/petroleum ether [40/60] 1:1).

$^1$H NMR (200 MHz, CDCl$_3$, TMS): δ=[0.72–0.90 (m), 1.11–1.27 (m), 1.40–1.59 (m) alkyl radical, 30H], 1.91 (s, NH, 1H), 2.49–2.80 (m, NCCH$_2$COO and CH$_2$N, 4H), 3.57 (t, NCH 1H), 3.88–4.10 (m, CH$_2$O, 4H).

$^{13}$C NMR (200 MHz, CDCl$_3$, TMS): δ=11.29, 11.47, 14.39, 23.33, 23.74, 24.07, 24.10, 29.27, 29.51, 30.53, 30.71, 38.48, 39.06, 39.09, 47.67, 57.83 (CH), 67.53 (CH$_2$), 67.72 (CH$_2$), 171.40 (C$_q$), 174.08 (C$_q$)

(104)

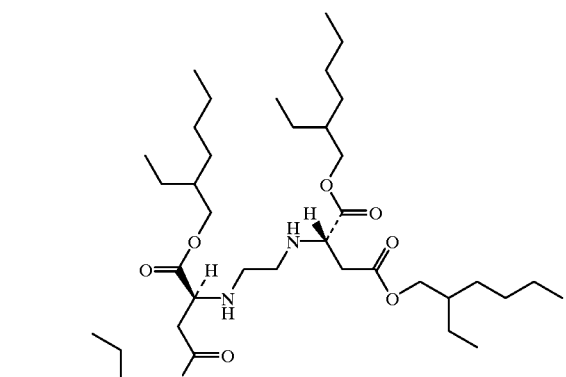

[S,S]-configuration

EXAMPLE 5

[S,S]-Ethylenediaminedisuccinic acid tetraisopropyl ester

Isopropanol (150.0 g, 2.5 mol) is placed in a vessel and thionyl chloride (14.3 g, 0.12 mol) is added dropwise at −5 to 5° C. [S,S]-Ethylenediaminesuccinic acid (5.84 g, 0.02 mol) is added in portions to the reaction mixture. The reaction mixture is slowly heated to room temperature and then for about 24 h to 60° C. Crystals of the tetraester hydrochloride of formula (105) form after cooling which are then collected by filtration and washed with 50 ml of methyl-tertbutyl ether.

After stirring the filter cake into a mixture of ice/ammonia solution it is worked up as described in Example 1. Removal of the solvent under vacuum (60° C.) gives the slightly contaminated tetraester in the form of a yellowish oil (yield: 1.71 g (19% of theory).

The product can be purified by column chromatography (silica gel G60, ethyl acetate/petroleum ether [40/60]/ethanol (9:1:0.5).

$^1$H NMR (200 MHz, CDCl$_3$, TMS): δ=1.15–1.38 (m, CH$_3$, 12H), 1.99 (s, NH, 1H), 2.54–2.85 NCCH$_2$COO and CH$_2$N, 4H), 3.58 (t, NCH, 1H), 4.93–5.12 (m, OCH, 2H).

$^{13}$C NMR (200 MHz, CDCl$_3$, TMS): δ=22.11 (CH$_3$), 22.15 (CH$_3$), 22.21 (CH$_3$), 38.72 (CH$_2$), 47.60 (CH$_2$), 57.99 (CH), 68.41 (CH), 68.85 (CH), 170.72 (C$_q$), 173.41 (C$_q$)

(105)

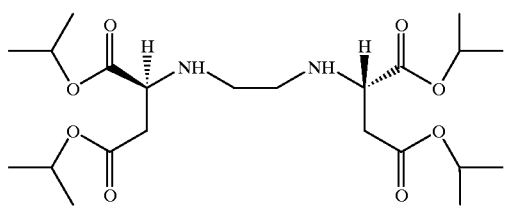

[S,S]-configuration

EXAMPLE 6

[S,S]-Ethylenediaminedisuccinic acid tetrabutyl ester n-Butanol (200 g, 2.7 mol) is placed in a vessel and thionyl chloride (14.3 g, 0.12 mol) is added dropwise at −5 to 5°C. [S,S]-Ethylenediaminedisuccinic acid (5.84 g, 0.02 mol) is added in portions to the reaction mixture. The reaction mixture is slowly heated to room temperature and then for another 48 h to 60° C. The suspension first turns into a solution and after some time the tetraester separates as hydrochloride in the form of white crystals. The mixture is cooled to room temperature and, after addition of 50 ml of methyl-tert-butyl ether, filtered. The filter cake is washed with 50 ml of methyl-tertbutyl ether and briefly dried by suction.

After stirring the filter cake into ice/ammonia solution, working up is carried out as described in Example 1, giving the tetraester of formula (106) in the form of a slightly yellowish liquid. Yield: 5.0 g (48.45% of theory)

$^1$H NMR (200 MHz, CDCl$_3$, TMS): δ=0.80–0.95 (m, CH$_3$, 6H), 1.22–1.41 (m, alkyl-CH$_2$, 4H), 1.48–1.65 (m, alkyl-CH$_2$, 4H), 1.94 (s, NH, 1H), 2.59–2.81 (m, NCCH2COO and CH$_2$N, 4H), 3.57 (t, NH, 1H), 3.98–4.16 (m, OCH$_2$).

$^{13}$C NMR (200 MHz, CDCl$_3$, TMS): δ=13.99 (CH$_3$), 19.42 (CH$_2$), 19.61 (CH$_2$), 30.94 (CH$_2$), 30.95 (CH$_2$), 38.44 (CH$_2$), 47.56 (CH$_2$), 57.79 (CH), 64.88 (CH$_2$), 65.17 (CH$_2$), 171.26 (C$_q$), 173.94 (C$_q$).

(106)

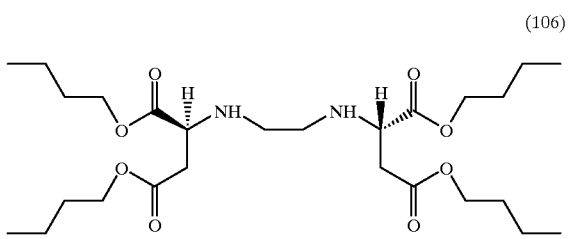

[S,S]-configuration

EXAMPLE 7

[S,S]-Ethylenediaminedisuccinic acid tetra-(2-butyl)ester

2-Butanol (200 g, 2.7 mol) is placed in a vessel and thionyl chloride (14.3 g, 0.12 mol) is added dropwise at −5 to 5° C. [S,S]-Ethylenediaminedisuccinic acid (5.84 g, 0.02 mol) is added in portions to the reaction mixture. The reaction mixture is slowly heated to room temperature and is then stirred for another 48 h at 60° C. The mixture is then heated to 80° C. and kept for 16 h at this temperature. The clear, colourless solution is cooled to 2° C. upon which the tetraester separates as hydrochloride in the form of white crystals. The mixture is filtered at 5° and the product is washed with 50 ml of methyl-tert-butyl ether. After stirring the filter cake into ice/ammonia solution, working up is carried out as described in Example 1. The tetraester of formula (107) is obtained in the form of a slightly yellow oil (yield: 0.9 g, 9% of theory) and can be purified by column chromatography (silica gel G60, ethyl acetate/petroleum ether [40/60] 8:2) to give a colourless oil.

$^1$H NMR (200 MHz, CDCl$_3$, TMS): δ=0.88–0.98 (m, CH2CH$_3$, 6H), 1.10–1.28 (m, CHCH$_3$, 6H), 1.42–1.68 (m, CH$_2$CH$_3$, 4H), 1.98 (s, NH, 1H), 2.52–2.88 (m, NCCH$_2$COO and CH$_2$N, 4H), 3.60 (t, NCH, 1H), 4.78–4.96 (m, CH$_2$N, 2H).

$^{13}$C NMR (200 MHz, CDCl$_3$, TMS): δ=10.46 (CH$_3$), 10.51 (CH$_3$), 20.17 (CH$_3$), 20.28 (CH$_3$), 29.54 (CH$_2$), 29.56 (CH$_2$), 39.18 (CH2), 48.1 (CH$_2$), 58.53 (CH), 73.39 (CH), 73.88 (CH), 171.30 (C$_q$) 174.01 (C$_q$).

(107)

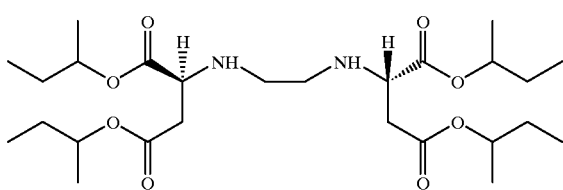

[S,S]-configuration

EXAMPLE 8

[S,S]-Ethylenediaminedisuccinic acid tetra(isobutyl) ester

Isobutanol (200 g, 2.7 mol) is placed in a vessel and thionyl chloride (14.3 g, 0.12 mol) is then added dropwise at −5 to 5° C. [S,S]-Ethylenediaminedisuccinic acid (5.84 g, 0.02 mol) is added in portions to the reaction mixture. The reaction mixture is slowly heated to room temperature and is then stirred for another 41 h at 60° C. The suspension first turns into a solution and after some time the tetraester separates as hydrochloride in the form of white crystals. The mixture is cooled to room temperature and filtered, and the filter cake is washed with 50 ml of methyl-tert-butyl ether.

After stirring the filter cake into ice/ammonia solution, the mixture is worked up as described in Example 1. The tetraester of formula (108) is obtained in the form of a slightly yellow oil (yield: 6.8 g, 66% of theory) and can be purified by column chromatography (silica gel G60, ethyl acetate/petroleum ether [40/60] 8:2) to give a colourless oil.

$^1$H NMR (200 MHz, CDCl$_3$, TMS): δ=0.84–1.01 (m, CH$_3$, 12H), 1.84–2.08 (m, NH and CH$_3$C$\underline{H}$, 3H), 2.55–2.88 (m, NCCH$_2$COO and CH$_2$N, 4H), 3.65 (t, NCH, 1H), 3.84–3.96 (m, OCH$_2$, 4H).

$^{13}$C NMR (200 MHz, CDCl$_3$, TMS): δ=18.39 (CH$_3$), 26.99, 27.03, 37.43 (CH$_2$), 46.61 (CH$_2$), 56.80 (CH), 70.15 (CH$_2$), 70.41 (CH$_2$), 170.24 (C$_q$), 172.92(C$_q$)

(108)

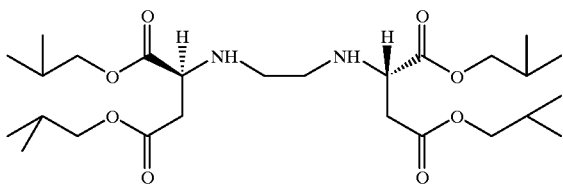

[S,S]-configuration

EXAMPLE 9

Microbiological Test

Medium
Casein soybean flour peptone agar (Merck)
Casein soybean flour peptone broth (Merck)
Test germs
*Staphylococcus aureus* ATCC 9144
*Corynebacterium xerosis* ATCC 373
*Escherichia coli* NCTC 8196
Preparation of the Germ Suspensions The test germs are cultivated overnight (about 18 h) at 37° C. in Caso-Broth (5 ml test tubes). The germ count of the overnight cultivation is determined by the spiralometer method and must be between $10^8$–$10^9$ KBE/ml.

The culture is diluted to about $10^7$ KBE/ml with 0.85% NaCl solution, pH 7.2.

Ground Layer

Petri dishes are filled with about 18 ml of sterile nutrient agar which is allowed to solidify.

Top Layer 3.5 ml of the germ dilution in 0.85% NaCl are pipetted into 500 ml of still liquid agar which is cooled in a water bath to 47° C. and homogenised.

6 ml of the germ-infested agar are evenly distributed on the solidified ground layer. After a drying and storage time of about 24 hours at 4° C. the dishes are ready for the test.

Drop Amount 100 μl of a 1% solution of the tetraester of formula (104) in abs. ethanol are pipetted into the centre of the dish and are dried for about 30 minutes at room temperature (the substances run into zones of about 20–30 mm).

Results of the Agar Diffusion Test

After a 48 h incubation of the agar dishes at 37° C., the growth of the test substances in the drop zone is assessed.

| Test sample | *Staphylococcus aureus* ATCC 9144 | *Corynebacterium xerosis* ATCC 373 | *Escherichia coli* NCTC 8196 |
|---|---|---|---|
| EtOH abs. (control) | no inhibition | no inhibition | no inhibition |
| [S,S]-ethylene-diaminedisuccinic acid tetra(isooctyl) ester 1% in EtOH | no inhibition | inhibition | no inhibition |
| ethylenediamine-disuccinic acid tetra(isooctyl)ester (isomer mixture) 1.0% in EtOH | no inhibition | inhibition | no inhibition |

A selective inhibition of Corynebacterium xerosis ATCC 373 is found.

What is claimed is:

1. A diester amine adduct of formula

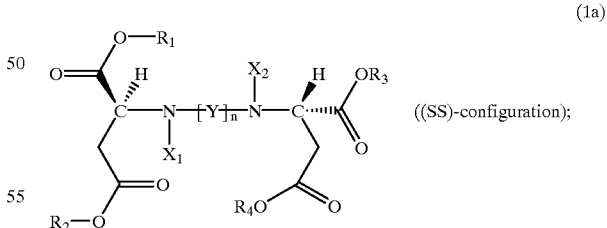

((SS)-configuration); (1a)

((RR)-configuration); or (1b)

-continued

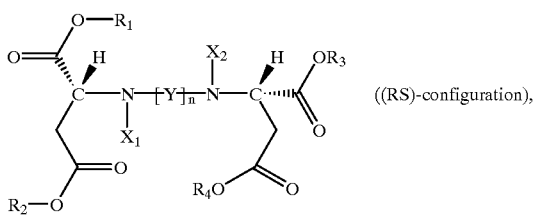

((RS)-configuration), wherein
R$_1$, R$_2$, R$_3$, R$_4$ are each independently of one another C$_4$–C$_{22}$alkyl; C$_2$–C$_{22}$alkenyl; or C$_5$–C$_7$cycloalkyl;
X$_1$ and X$_2$ are each independently of the other hydrogen, C$_1$–C$_4$alkyl; C$_2$–C$_4$hydroxyalkyl or C$_2$–C$_4$hydroxyhaloalkyl;
Y is a radical of formula (1b)

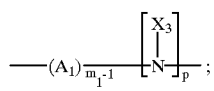

A$_1$ is C$_2$–C$_3$alkylene or 2-hydroxy-n-propylene;
X$_3$ is hydrogen; C$_1$–C$_4$alkyl, C$_2$–C$_4$hydroxyalkyl; or C$_2$–C$_4$hydroxyhaloalkyl;
m$_1$ is 1 or 2; and
n is an integer from 1 to 4;
p is 0 or 1;
which adduct may be in the form of a free base, acid, acid salt or quaternary ammonium salt.

2. A diester amine adduct according to claim 1, wherein in formula (1)
A$_1$ is C$_2$–C$_3$alkylene;
m is 2; and
p is 0.

3. A diester amine adduct according to claim 1, wherein X$_1$ and X$_2$ are hydrogen.

4. A diester amine adduct according to claim 1, wherein R$_1$, R$_2$, R$_3$ and R$_4$ are C$_4$–C$_{22}$alkyl.

5. A method of complexing metal ions selected from calcium, iron, copper and magnesium, which comprises adding an effective complexing amount of the diester amine adduct of formula (1a), (1b) or (1c) as defined in claim 1, as complex former, to the environment of the metal salt.

6. A method according to claim 5, which comprises adding the compound of formula (2) in foods and beverages, in derusting and decalcification baths, as an additive in liquids for cooling-water circuits, in personal-care products, as bleaching stabilisers and in cleaning agents and detergents.

7. A method according to claim 5, which comprises using the compound of formula (2) in body-care products.

8. A method according to claim 7, which comprises using the compound of formula (2) in deodorants.

9. A body-care product, which comprises 0.01 to 15% by weight of the diester amine adduct of formula

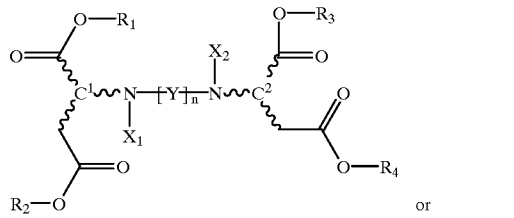

or

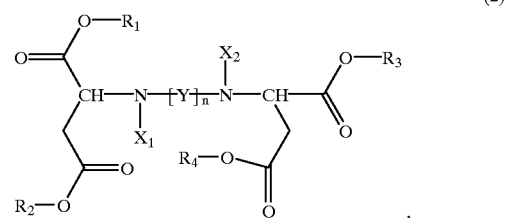

wherein
R$_1$, R$_2$, R$_3$, R$_4$, X$_1$ and X$_2$, Y and n are as defined in claim 1.

* * * * *

UNITED STATES PATENT AND TRADEMARK OFFICE
CERTIFICATE OF CORRECTION

PATENT NO. : 6,369,268 B1
DATED : April 9, 2002
INVENTOR(S) : Thomas Ehlis et al.

It is certified that error appears in the above-identified patent and that said Letters Patent is hereby corrected as shown below:

<u>Title page,</u>
Item [75], should read:
-- Inventors: Thomas Ehlis, Freiburg; Peter Fankhauser; Ettingen; Dietmar Hüglin; Eimeldingen, all of (DE) --.

Signed and Sealed this

Sixteenth Day of July, 2002

*Attest:*

*Attesting Officer*

JAMES E. ROGAN
*Director of the United States Patent and Trademark Office*